United States Patent [19]

Edwards et al.

[11] Patent Number: 5,519,022
[45] Date of Patent: May 21, 1996

[54] α, α DIALKYLBENZYL DERIVATIVES

[75] Inventors: Philip N. Edwards, Bramhall; David Waterson, Bollington, both of England

[73] Assignees: Imperial Chemical Industries Plc, London, United Kingdom; ICI Pharma, Cergy Cedex, France

[21] Appl. No.: 149,803

[22] Filed: Nov. 10, 1993

Related U.S. Application Data

[63] Continuation of Ser. No. 853,277, Mar. 18, 1992, Pat. No. 5,288,742.

[30] Foreign Application Priority Data

Mar. 21, 1991 [EP] European Pat. Off. .............. 91400772

[51] Int. Cl.⁶ .................... C07D 251/00; C07D 215/04; A01N 43/64; A01N 43/42

[52] U.S. Cl. .......... 514/243; 514/249; 514/259; 514/311; 514/312; 514/314; 544/180; 544/183; 544/235; 544/236; 544/253; 544/279; 544/350; 544/353; 544/354; 544/355; 544/356; 546/118; 546/119; 546/120; 546/122; 546/123; 546/153; 546/155; 546/156; 546/164; 546/168; 546/170; 546/173; 546/174; 546/176; 546/177; 546/178; 546/179; 546/180

[58] Field of Search ..................... 544/180, 183, 544/235, 236, 253, 279, 350, 353, 354, 355, 356; 546/153, 155, 156, 164, 168, 170, 173, 174, 176, 177, 178, 179, 180, 118, 119, 120, 122, 123; 514/243, 249, 259, 311, 312, 314

[56] References Cited

U.S. PATENT DOCUMENTS

| | | | |
|---|---|---|---|
| 3,661,917 | 5/1972 | Kaiser et al. | 546/173 |
| 3,743,737 | 7/1973 | Kaiser et al. | 546/173 |
| 4,377,712 | 3/1983 | Foster et al. | 568/635 |
| 4,419,122 | 10/1983 | Swithenbank | 568/635 |
| 4,567,184 | 1/1986 | Musser et al. | 514/277 |
| 4,625,034 | 11/1986 | Neiss et al. | 546/152 |
| 4,631,287 | 12/1986 | Chakraborty et al. | 514/307 |
| 4,725,619 | 2/1916 | Chakraborty et al. | 514/442 |
| 4,728,668 | 3/1988 | Chakraborty et al. | 514/464 |
| 4,794,188 | 12/1988 | Musser et al. | 546/152 |
| 4,839,369 | 6/1989 | Youssefyeh et al. | 514/314 |
| 4,876,346 | 10/1989 | Musser et al. | 525/146 |
| 4,918,081 | 4/1990 | Huang et al. | 514/314 |
| 4,920,130 | 4/1990 | Huang et al. | 514/314 |
| 4,920,131 | 4/1990 | Huang et al. | 514/314 |
| 4,920,132 | 4/1990 | Huang et al. | 546/173 |
| 4,920,133 | 4/1990 | Huang et al. | 546/153 |
| 5,098,930 | 3/1992 | Edwards | 514/459 |
| 5,098,932 | 3/1992 | Hamon | 514/462 |
| 5,105,020 | 4/1992 | Girodeau | 568/633 |
| 5,126,365 | 6/1992 | Bird | 514/451 |
| 5,132,328 | 7/1992 | Girodeau | 514/716 |

FOREIGN PATENT DOCUMENTS

| | | |
|---|---|---|
| 0110405 | 6/1984 | European Pat. Off. . |
| 0181568 | 5/1986 | European Pat. Off. . |
| 0190722 | 8/1986 | European Pat. Off. . |
| 0200101 | 12/1986 | European Pat. Off. . |
| 0271287 | 6/1988 | European Pat. Off. . |
| 0349062 | 6/1989 | European Pat. Off. . |
| 414076 | 2/1991 | European Pat. Off. . |

*Primary Examiner*—C. Warren Ivy
*Assistant Examiner*—Raymond Covington
*Attorney, Agent, or Firm*—Cushman Darby & Cushman

[57] ABSTRACT

The invention concerns α,α-dialkylbenzyl derivatives of the formula I

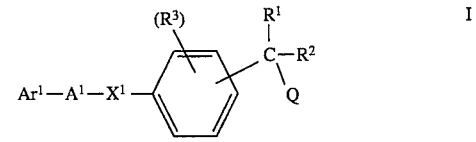

wherein $Ar^1$ is phenyl or naphthyl, or a 10-membered bicyclic heterocyclic moiety containing one or two nitrogen heteroatoms and optionally containing a further heteroatom selected from nitrogen, oxygen and sulphur;

$A^1$ is a direct link to $X^1$ or is (1–3C)alkylene;

$X^1$ is oxy, thio, sulphinyl or sulphonyl;

the phenylene group may optionally bear one or two substituents $R^3$;

each of $R^1$ and $R^2$, which may be the same or different is (1–4C)alkyl, (2–4C)alkenyl, (2–4C)alkynyl, fluoro-(1–4C)alkyl, phenyl or phenyl-(1–4C)alkyl, provided that both of $R^1$ and $R^2$ are not methyl or fluoromethyl; and Q is cyano, amino, nitro, formyl, (1–4C)alkoxy, thiazolyl or (2–4C)alkanoyl;

or a pharmaceutically-acceptable salt thereof;
processes for their manufacture; pharmaceutical compositions containing them and their use as 5-lipoxygenase inhibitors.

7 Claims, No Drawings

# α, α DIALKYLBENZYL DERIVATIVES

This is a continuation of application Ser. No. 07/853,277, filed Mar. 18, 1992 now U.S. Pat. No. 5,288,742.

This invention concerns α,α-dialkylbenzyl derivatives and more particularly α,α-dialkylbenzyl derivatives which are inhibitors of the enzyme 5-lipoxygenase (hereinafter referred to as 5-LO). The invention also concerns processes for the manufacture of said α,α-dialkylbenzyl derivatives and pharmaceutical compositions containing them. Also included in the invention is the use of said α,α-dialkylbenzyl derivatives in the treatment of various inflammatory and/or allergic diseases in which the direct or indirect products of 5-LO catalysed oxidation of arachidonic acid are involved, and the production of new medicaments for such use.

As stated above the α,α-dialkylbenzyl derivatives described hereinafter are inhibitors of 5-LO, which enzyme is known to be involved in catalysing the oxidation of arachidonic acid to give rise via a cascade process to the physiologically active leukotrienes such as leukotriene $B_4$ ($LTB_4$) and the peptido-lipid leukotrienes such as leukotriene $C_4$ ($LTC_4$) and leukotriene $D_4$ ($LTD_4$) and various metabolites.

The biosynthetic relationship and physiological properties of the leukotrienes are summarised by G. W. Taylor and S. R. Clarke in *Trends in Pharmacological Sciences*, 1986, 7, 100–103. The leukotrienes and their metabolites have been implicated in the production and development of various inflammatory and allergic diseases such as inflammation of the joints (especially rheumatoid arthritis, osteoarthritis and gout), inflammation of the gastrointestinal tract (especially inflammatory bowel disease, ulcerative colitis and gastritis), skin disease (especially psoriasis, eczema and dermatitis) and respiratory disease (especially asthma, bronchitis and allergic rhinitis), and in the production and development of various cardiovascular and cerebrovascular disorders such as myocardial infarction, angina and peripheral vascular disease. In addition the leukotrienes are mediators of inflammatory diseases by virtue of their ability to modulate lymphocyte and leukocyte function. Other physiologically active metabolites of arachidonic acid, such as the prostaglandins and thromboxanes, arise via the action of the enzyme cyclooxygenase on arachidonic acid.

It is known from European Patent Application No. 0181568 that 3-(quinolin-2-ylmethoxy)phenylacetic acid and 2-[3-(quinolin-2-ylmethoxy)phenyl]propionic acid and certain methyl or ethyl esters thereof possess anti-inflammatory properties.

It is also disclosed in European Patent Application No. 0414076 that further 4-(quinolin-2-ylmethoxy)phenylacetic acid derivatives are inhibitors of the enzyme lipoxygenase.

We have now discovered that the acid group is not mandatory and may be replaced by several other groups.

Thus we have now discovered that certain α,α-dialkylbenzyl derivatives are effective as inhibitors of the enzyme 5-LO and thus of leukotriene biosyntheses. Thus, such compounds are of value as therapeutic agents in the treatment of, for example, allergic conditions, psoriasis, asthma, cardiovascular and cerebrovascular disorders, and/or inflammatory and arthritic conditions, mediated alone or in part by one or more leukotrienes.

According to the invention there is provided an α,α-dialkylbenzyl derivative of the formula I (set out hereinafter) wherein $Ar^1$ is phenyl or naphthyl, or a 10-membered bicyclic heterocyclic moiety containing one or two nitrogen heteroatoms and optionally containing a further heteroatom selected from nitrogen, oxygen and sulphur, and $Ar^1$ may optionally bear up to four substituents selected from halogeno, hydroxy, cyano, oxo, thioxo, (1–4C)alkyl, (1–4C)alkoxy, fluoro-(1–4C)alkyl, phenyl, benzoyl, phenyl-(1–4C)alkyl, α,α-difluorobenzyl, α-hydroxybenzyl and α-[(1–4C)alkoxy]benzyl and wherein said phenyl substituent or any of said substituents which contain a phenyl group may optionally bear a substituent selected from halogeno, (1–4C)alkyl and (1–4C)alkoxy;

$A^1$ is a direct link to $X^1$ or is (1–3C)alkylene;

$X^1$ is oxy, thio, sulphinyl or sulphonyl;

the phenylene group may optionally bear one or two substituents $R^3$ selected from halogeno, hydroxy, amino, nitro, cyano, carbamoyl, ureido, (1–4C)alkyl, (1–4C)alkoxy and fluoro-(1–4C)alkyl;

each of $R^1$ and $R^2$, which may be the same or different, is (1–4C)alkyl (2–4C)alkenyl, (2–4C)alkynyl, fluoro-(1–4C)alkyl, phenyl or phenyl-(1–4C)alkyl and wherein said phenyl or phenyl-(1–4C)alkyl group may optionally bear one or two substituents selected from halogeno, trifluoromethyl, (1–4C)alkyl and (1–4C)alkoxy, provided that both of $R^1$ and $R^2$ are not methyl or fluoromethyl; and Q is cyano, amino, nitro, formyl, (1–4C)alkoxy, thiazolyl or (2–4C)alkanoyl;

or a pharmaceutically-acceptable salt thereof.

According to a further aspect of the invention there is provided an α,α-dialkylbenzyl derivative of the formula I wherein $Ar^1$ is phenyl or naphthyl, or a 10-membered bicyclic heterocyclic moiety containing one or two nitrogen heteroatoms and optionally containing a further heteroatom selected from nitrogen, oxygen and sulphur, and $Ar^1$ may optionally bear up to four substituents selected from halogeno, hydroxy, cyano, oxo, thioxo, (1–4C)alkyl, (1–4C)alkoxy, fluoro-(1–4C)alkyl, phenyl, benzoyl, phenyl-(1–4C)alkyl, α,α-difluorobenzyl, α-hydroxybenzyl and α-[(1–4C)alkoxy]benzyl and wherein said phenyl substituent or any of said substituents which contain a phenyl group may optionally bear a substituent selected from halogeno, (1–4C)alkyl and (1–4C)alkoxy;

$A^1$ is a direct link to $X^1$ or is (1–3C)alkylene;

$X^1$ is oxy, thio, sulphinyl or sulphonyl;

the phenylene group may optionally bear one or two substituents $R^3$ selected from halogeno, hydroxy, amino, nitro, cyano, carbamoyl, ureido, (1–4C)alkyl, (1–4C)alkoxy and fluoro-(1–4C)alkyl;

each of $R^1$ and $R^2$, which may be the same or different is (2–4C)alkyl, (2–4C)alkenyl, (2–4C)alkynyl or fluoro-(2–4C)alkyl; and Q is cyano, amino, nitro, formyl, (1–4C)alkoxy or thiazolyl;

or a pharmaceutically-acceptable salt thereof.

The chemical formulae referred to herein by Roman numerals are set out for convenience on a separate sheet hereinafter.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of the formula I defined above may exhibit the phenomenon of tautomerism and any formula drawing presented herein may represent only one of the possible tautomeric forms, the invention includes in its definition any tautomeric form of a compound of the formula I which possesses the property of inhibiting 5-LO and is not to be limited merely to any one tautomeric form utilised within the formulae drawings.

It is further to be understood that, insofar as certain of the compounds of formula I defined above may exist in optically active or racemic forms by virtue of one or more substituents containing an asymmetric carbon atom, the invention includes in its definition any such optically active or racemic form which possesses the property of inhibiting 5-LO. The synthesis of optically active forms may be carried out by standard techniques of organic chemistry well known in the art, for example by synthesis from optically active starting materials or by resolution of a racemic form. Similarly, inhibitory properties against 5-LO may be evaluated using the standard laboratory techniques referred to hereinafter.

Suitable values for the generic terms referred to above include those set out below.

A suitable value for $Ar^1$ when it is naphthyl is, for example 1-naphthyl or 2-naphthyl.

A suitable value for $Ar^1$ when it is a 10-membered bicyclic heterocyclic moiety containing one or two nitrogen heteroatoms and optionally containing a further heteroatom selected from nitrogen, oxygen and sulphur is, for example, a 10-membered benzo-fused heterocyclic moiety such as quinolyl, isoquinolyl, cinnolinyl, quinazolinyl, quinoxalinyl, 4H-1,4-benzoxazinyl or 4H-1,4-benzothiazinyl, or a hydrogenated derivative thereof such as 1,2-dihydroquinolyl, 1,2,3,4-tetrahydroquinolyl, 1,2-dihydroisoquinolyl, 2,3-dihydro-4H-1,4-benzoxazinyl or 2,3-dihydro-4H-1,4-benzothiazinyl; or, for example, a 10-membered pyrido-fused heterocyclic moiety such as 1,7-naphthyridinyl, 1,8-naphthyridinyl, pyrido[2,3-d]pyrimidinyl, pyrido[2,3-b]pyrazinyl, 4H-pyrido[3,2-b][1,4]oxazinyl and 4H-pyrido[3,2-b][1,4]thiazinyl, or a hydrogenated derivative thereof.

The heterocyclic moiety may be attached through any available position including from either of the two rings of the bicyclic heterocyclic moiety and including through an available nitrogen atom. The heterocyclic moiety may bear a suitable substituent such as, for example, a (1–4C)alkyl, phenyl, benzoyl or phenyl-(1–4C)alkyl substituent on an available nitrogen atom.

Suitable values for substituents which may be present on $Ar^1$, on the phenylene group, on the phenyl substituent on $Ar^1$ or on any of the substituents on $Ar^1$ which contain a phenyl group or on $R^1$ or $R^2$ when each is phenyl or phenyl-(1–4C)alkyl, include, for example:

for halogeno: fluoro, chloro, bromo and iodo;

for (1–4C)alkyl: methyl, ethyl, propyl, isopropyl, butyl, isobutyl, sec-butyl and tert-butyl;

for (1–4C)alkoxy: methoxy, ethoxy, propoxy, isopropoxy and butoxy;

for fluoro-(1–4C)alkyl: fluoromethyl, difluoromethyl, trifluoromethyl, 2-fluoroethyl, 2,2,2-trifluoroethyl and pentafluoroethyl;

for phenyl-(1–4C)alkyl: benzyl, phenethyl, 3-phenylpropyl and α-methylbenzyl;

for α-[(1–4C)alkoxy]benzyl: α-methoxybenzyl and α-ethoxybenzyl.

A suitable value for $A^1$ when it is (1–3C)alkylene is, for example, methylene, ethylene or trimethylene.

A suitable value for the phenylene group is, for example, 1,3-phenylene or 1,4-phenylene.

A suitable value for $R^1$ or $R^2$ when it is (1–4C)alkyl is, for example, methyl, ethyl, propyl, isopropyl or butyl; when it is (2–4C)alkenyl is, for example, vinyl of allyl; when it is (2–4C)alkynyl is, for example, ethynyl or 2-propynyl; when it is fluoro-(1–4C)alkyl is, for example, fluoromethyl, 2-fluoroethyl, 2,2,2-trifluoroethyl or pentafluoroethyl; and when it is phenyl-(1–4C)alkyl is, for example, benzyl or phenethyl.

A suitable value for Q when it is (1–4C)alkoxy is, for example, methoxy, ethoxy or propoxy; when it is thiazolyl is, for example, 2-, 4- or 5-thiazolyl; and when it is (2–4C)alkanoyl is, for example, acetyl, propionyl or butyryl.

A suitable pharmaceutically-acceptable salt of a novel compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a novel compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular compounds of the invention are, for example, α,α-dialkylbenzyl derivatives of the formula I wherein:

(a) $Ar^1$ is phenyl or naphthyl which may optionally bear one, two or three substituents selected from any of those substituents on $Ar^1$ defined hereinbefore other than oxo and thioxo; and $A^1, X^1, R^1, R^2, R^3$, and Q have any of the meanings defined hereinbefore or in this section concerning particular compounds of the invention;

(b) $Ar^1$ is phenyl or naphth-2-yl which may optionally bear one or two substituents selected from fluoro, chloro, methyl, ethyl, isopropyl, tert-butyl, methoxy, trifluoromethyl, phenyl, benzoyl, benzyl, α,α-difluorobenzyl and α-methoxybenzyl, and wherein said phenyl, benzoyl, benzyl, α,α-difluorobenzyl or α-methoxybenzyl substituents may optionally bear a substituent selected from fluoro, chloro, methyl and methoxy; and $A^1, X^1, R^1, R^2, R^3$ and Q have any of the meanings defined hereinbefore or in this section concerning particular compounds of the invention;

(c) $Ar^1$ is a 10-membered benzo-fused heterocyclic moiety containing one or two nitrogen heteroatoms and optionally containing a further heteroatom selected from oxygen and sulphur, which heterocyclic moiety may optionally bear one or two oxo or thioxo substituents and up to two further substituents selected from any of those substituents on $Ar^1$ defined hereinbefore other than oxo or thioxo; and $A^1, X^1, R^1, R^2, R^3$ and Q have any of the meanings defined hereinbefore or in this section concerning particular compounds of the invention;

(d) $Ar^1$ is quinolyl, 1,2-dihydroquinolyl, isoquinolyl, 1,2-dihydroisoquinolyl, quinoxalinyl, 2,3-dihydro-4H-1,4-benzoxazinyl or 2,3-dihydro-4H-1,4-benzothiazinyl, which may optionally bear one or two oxo or thioxo substituents and up to two further substituents selected from any of those substituents on $Ar^1$ defined hereinbefore other than oxo or thioxo; and $A^1, X^1, R^1, R^2, R^3$ and Q have any of the meanings defined hereinbefore or in this section concerning particular compounds of the invention;

(e) $Ar^1$ is quinolyl, 1,2-dihydroquinolyl, 1,2,3,4-tetrahydroquinolyl or 2,3-dihydro-4H-1,4-benzoxazinyl which may optionally bear one oxo or thioxo substituent and up to two further substituents selected from any of those substituents on $Ar^1$ defined hereinbefore other than oxo or thioxo; and $A^1$, $X^1$, $R^1$, $R^2$, $R^3$ and Q have any of the meanings defined hereinbefore or in this section concerning particular compounds of the invention;

(f) $Ar^1$ is 2-quinolyl, 3-quinolyl, 6-quinolyl, 7-quinolyl, 3-isoquinolyl, 6-isoquinolyl, 7-isoquinolyl, 2-quinoxalinyl, 6-quinoxalinyl, 4H-1,4-benzoxazin-6-yl or 4H-1,4-benzothiazin-6-yl, which may optionally bear one or two substituents selected from any of those substituents on $Ar^1$ defined hereinbefore other than oxo or thioxo; and $A^1$, $X^1$, $R^1$, $R^2$, $R^3$ and Q have any of the meanings defined hereinbefore or in this section concerning particular compounds of the invention;

(g) $Ar^1$ is 2-oxo-1,2-dihydroquinolinyl, 3-oxo-2,3-dihydro-4H-1,4-benzoxazinyl or 3-oxo-2,3-dihydro-4H-1,4-benzothiazinyl, or the corresponding thioxo derivatives thereof, which may optionally bear up to three substituents selected from any of those substituents on $Ar^1$ defined hereinbefore other than oxo or thioxo; and $A^1$, $X^1$, $R^1$, $R^2$, $R^3$ and Q have any of the meanings defined hereinbefore or in this section concerning particular compounds of the invention;

(h) $Ar^1$ is 2-oxo-1,2-dihydroquinolinyl, 2-thioxo-1,2-dihydroquinolinyl, 2-oxo-1,2,3,4-tetrahydroquinolinyl, 2-thioxo-1,2,3,4-tetrahydroquinolinyl or 3-oxo-2,3-dihydro-4H-1,4-benzoxazinyl which may optionally bear up to three substituents selected from any of those substituents on $Ar^1$ defined hereinbefore other than oxo or thioxo; and $A^1$, $X^1$, $R^1$, $R^2$, $R^3$ and Q have any of the meanings defined hereinbefore or in this section concerning particular compounds of the invention;

(i) $Ar^1$ is 2-oxo-1,2-dihydroquinolin-3-yl, 2-oxo-1,2-dihydroquinolin-6-yl, 2-oxo-1,2-dihydroquinolin-7-yl, 3-oxo-2,3-dihydro-4H-1,4-benzoxazin-7-yl or 3-oxo-2,3-dihydro-4H-1,4-benzothiazin-7-yl, which may optionally bear up to three substituents selected from any of those substituents on $Ar^1$ defined hereinbefore other than oxo or thioxo; and $A^1$, $X^1$, $R^1$, $R^2$, $R^3$ and Q have any of the meanings defined hereinbefore or in this section concerning particular compounds of the invention;

(j) $Ar^1$ is a direct link to $X^1$, and $X^1$ is oxy, thio, sulphinyl or sulphonyl; and $Ar^1$, $R^1$, $R^2$, $R^3$ and Q have any of the meanings defined hereinbefore or in this section concerning particular compounds of the invention;

(k) $A^1$ is methylene and $X^1$ is oxy, thio, sulphinyl or sulphonyl; and $Ar^1$, $R^1$, $R^2$, $R^3$ and Q have any of the meanings defined hereinbefore or in this section concerning particular compounds of the invention;

(l) the phenylene group is 1,3-phenylene which may optionally bear one or two substituents $R^3$ selected from fluoro, chloro, hydroxy, amino, nitro, ureido methyl methoxy and trifluoromethyl; and $Ar^1$, $A^1$, $X^1$, $R^1$, $R^2$ and Q have any of the meanings defined hereinbefore or in this section concerning particular compounds of the invention;

(m) each of $R^1$ and $R^2$, which may be the same or different is ethyl propyl, allyl, 2-fluoroethyl or 2 2,2-trifluoroethyl; and $Ar^1$, $A^1$, $X^1$, $R^3$ and Q have any of the meanings defined hereinbefore or in this section concerning particular compounds of the invention;

(n) each of $R^1$ and $R^2$, which may be the same or different is methyl, ethyl, propyl, allyl, fluoromethyl, 2-fluoroethyl or benzyl and wherein said benzyl group may optionally bear one or two substituents selected from fluoro, chloro and trifluoromethyl, provided that both of $R^1$ and $R^2$ are not methyl or fluoromethyl; and $Ar^1$, $A^1$, $X^1$, $R^3$ and Q have any of the meanings defined hereinbefore or in this section concerning particular compounds of the invention;

(o) Q is cyano, amino, formyl, methoxy, ethoxy or 2-thiazolyl and $Ar^1$, $A^1$, $X^1$, $R^1$, $R^2$ and $R^3$ have any of the meanings defined hereinbefore or in this section concerning particular compounds of the invention;

(p) Q is cyano, amino, formyl, methoxy, ethoxy, propoxy, 2-thiazolyl, acetyl or propionyl; and $Ar^1$, $A^1$, $X^1$, $R^1$, $R^2$ and $R^3$ have any of the meanings defined hereinbefore or this section concerning particular compounds of the invention;

(q) Q is cyano, acetyl or propionyl; and $Ar^1$, $A^1$, $X^1$, $R^1$, $R^2$ and $R^3$ have any of the meanings defined hereinbefore or in this section concerning particular compounds of the invention;

(r) Q is methoxy, ethoxy or propoxy; and $Ar^1$, $A^1$, $X^1$, $R^1$, $R^2$ and $R^3$ have any of the meanings defined hereinbefore or in this section concerning particular compounds of the invention; and (s) Q is 2-thiazolyl; and $Ar^1$, $A^1$, $X^1$, $R^1$, $R^2$ and $R^3$ have any of the meanings defined hereinbefore or in this section concerning particular compounds of the invention.

or a pharmaceutically-acceptable salt thereof.

A preferred compound of the invention comprises an $\alpha,\alpha$-dialkylbenzyl derivative of the formula I wherein $Ar^1$ is phenyl which may optionally bear a substituent selected from fluoro, chloro, methyl, tert-butyl, phenyl, benzoyl, benzyl and $\alpha,\alpha$-difluorobenzyl and wherein said phenyl, benzoyl, benzyl or $\alpha,\alpha$-difluorobenzyl substituent may optionally bear a fluoro or chloro substituent, or $Ar^1$ is naphth-2-yl which may optionally bear a substituent selected from fluoro, chloro and methyl;

$A^1$ is a direct link to $X^1$, or is methylene;

$X^1$ is oxy, thio, sulphinyl or sulphonyl;

the phenylene group is 1,3-phenylene which may optionally bear one substituent $R^3$ selected from fluoro, chloro and trifluoromethyl;

each of $R^1$ and $R^2$, which may be the same or different is methyl, ethyl propyl allyl or benzyl provided that both of $R^1$ and $R^2$ are not methyl; and Q is cyano, methoxy, ethoxy, 2-thiazolyl, acetyl or propionyl;

or a pharmaceutically-acceptable salt thereof.

A further preferred compound of the invention comprises an $\alpha,\alpha$-dialkylbenzyl derivative of the formula I wherein $Ar^1$ is 2-quinolyl, 6-quinolyl, 6-quinoxazinyl, 2-oxo-1,2-dihydroquinolin-3-yl, 2-oxo-1,2-dihydroquinolin-6-yl, 2-oxo-1,2-dihydroquinolin-7-yl, 3-oxo-2,3-dihydro-4H-1,4-benzoxazin-7-yl or 3-oxo-2,3-dihydro-4H-1,4-benzothiazin-7-yl, which may optionally bear one, two or three substituents selected from fluoro, chloro, methyl, ethyl, 2-fluoroethyl, phenyl and benzyl;

$A^1$ is a direct link to $X^1$, or is methylene;

$X^1$ is oxy, thio, sulphinyl or sulphonyl;

the phenylene group is 1,3-phenylene which may optionally bear one substituent $R^3$ selected from fluoro, chloro and trifluoromethyl;

each of $R^1$ and $R^2$, which may be the same or different is methyl, ethyl, propyl, allyl or benzyl, provided that both of $R^1$ and $R^2$ are not methyl; and Q is cyano, methoxy, ethoxy, 2-thiazolyl, acetyl or propionyl;

or a pharmaceutically-acceptable salt thereof.

A further preferred compound of the invention comprises an α,α-dialkylbenzyl derivative of the formula I wherein $Ar^1$ is naphth-2-yl, 1-methyl-2-oxo-1,2-dihydroquinolin-6-yl, 1-methyl-2-thioxo-1,2-dihydroquinolin-6-yl, 1-methyl-2-oxo-1,2,3,4-tetrahydroquinolin-6-yl or 4-methyl-3-oxo-2,3-dihydro-4H-1,4-benzoxazin-7-yl;

$A^1$ is a direct link to $X^1$ and $X^1$ is thio, or $A^1$ is methylene and $X^1$ is oxy;

the phenylene group bearing $R^3$ is 1,3-phenylene or 5-fluoro-1,3-phenylene;

each of $R^1$ and $R^2$ is ethyl; and

Q is cyano;

or a pharmaceutically-acceptable salt thereof.

A further preferred compound of the invention comprises an α,α-dialkylbenzyl derivative of the formula I wherein $Ar^1$ is naphth-2-yl, 2-quinolyl or 1-methyl-2-oxo-1,2-dihydroquinolin-6-yl;

$A^1$ is methylene and $X^1$ is oxy:

the phenylene group bearing $R^3$ is 1,3-phenylene or 5-fluoro-1,3-phenylene;

$R^1$ is ethyl or allyl;

$R^2$ is methyl, ethyl, allyl or benzyl; and

Q is cyano, methoxy, ethoxy, 2-thiazolyl or acetyl;

or a pharmaceutically-acceptable salt thereof.

A further preferred compound of the invention comprises an α,α-dialkylbenzyl derivative of the formula I wherein $Ar^1$ is naphth-2-yl, 2-quinolyl or 1-methyl-2-oxo-1,2-dihydroquinolin-6-yl;

$A^1$ is methylene and $X^1$ is oxy;

the phenylene group bearing $R^3$ is 1,3-phenylene or 5-fluoro-1,3-phenylene;

$R^1$ is ethyl or allyl;

$R^2$ is methyl, ethyl, allyl or benzyl; and

Q is cyano or acetyl;

or a pharmaceutically-acceptable salt thereof.

A further preferred compound of the invention comprises an α,α-dialkylbenzyl derivative of the formula I wherein $Ar^1$ is naphth-2-yl or 1-methyl-2-oxo-1,2-dihydroquinolin-6-yl;

$A^1$ is methylene and $X^1$ is oxy;

the phenylene group bearing $R^3$ is 1,3-phenylene or 5-fluoro-1,3-phenylene;

$R^1$ is ethyl or allyl;

$R^2$ is methyl, ethyl or allyl; and

Q is methoxy or ethoxy;

or a pharmaceutically-acceptable salt thereof.

A further preferred compound of the invention comprises an α,α-dialkylbenzyl derivative of the formula I wherein $Ar^1$ is naphth-2-yl or 1-methyl-2-oxo-1,2-dihydroquinolin-6-yl;

$A^1$ is methylene and $X^1$ is oxy;

the phenylene group bearing $R^3$ is 1,3-phenylene or 5-fluoro-1,3-phenylene;

$R^1$ is ethyl or allyl;

$R^2$ is methyl, ethyl or allyl; and

Q is 2-thiazolyl;

or a pharmaceutically-acceptable salt thereof.

A specific especially preferred compound of the invention is the following compound of The formula I, or a pharmaceutically-acceptable salt thereof:

2-ethyl-2-[3-(naphth-2-ylmethoxy)phenyl]butyronitrile, 2-ethyl-2-[3-(1-methyl-2-oxo-1,2-dihydroquinolin-6-ylmethoxy)phenyl]butyronitrile, 2-methyl-2-[3-(1-methyl-2-oxo-1,2-dihydroquinolin-6-ylmethoxy)phenyl]butyronitrile, 2,2-diallyl-2-[3-(1-methyl-2-oxo-1,2-dihydroquinolin-6-ylmethoxy)phenyl]acetonitrile or 3-ethyl-3-[3-(1-methyl-2-oxo-1,2-dihydroquinolin-6-ylmethoxy)phenyl]pentan-2-one.

A compound of the invention comprising an α,α-dialkylbenzyl derivative of the formula I, or a pharmaceutically-acceptable salt thereof, may be prepared by any process known to be applicable to the preparation of structurally-related compounds. Such procedures are provided as a further feature of the invention and are illustrated by the following representative examples in which, unless otherwise stated, $Ar^1$, $A^1$, $X^1$, $R^1$, $R^2$, $R^3$ and Q have any of the meanings defined hereinbefore.

(a) The coupling, preferably in the presence of a suitable base, of a compound of the formula $Ar^1$-$A^1$-$X^1$-H with a compound of the formula II wherein Z is a displaceable group; provided that, when there is an amino or hydroxy group in $Ar^1$ or on the phenylene group, or when Q is amino, any amino or hydroxy group may be protected by a conventional protecting group or alternatively any such group need not be protected, whereafter any undesired protecting group in $Ar^1$, the phenylene group or Q is removed by conventional means.

A suitable displaceable group Z is, for example, a halogeno or sulphonyloxy group, for example a fluoro, chloro, bromo, iodo, methanesulphonyloxy or toluene-R-sulphonyloxy group.

A suitable base for The coupling reaction is, for example, an alkali or alkaline earth metal carbonate, (1–4C)alkoxide, hydroxide or hydride, for example sodium carbonate, potassium carbonate, sodium ethoxide, potassium butoxide, sodium hydroxide, potassium hydroxide, sodium hydride or potassium hydride; or an organometallic base such as (1–4C)alkyl-lithium, for example n-butyl-lithium. The coupling reaction is conveniently performed in a suitable inert solvent or diluent, for example N,N-dimethylformamide, N,N-dimethylacetamide, N-methylpyrrolidin-2-one, dimethylsulphoxide, acetone, 1,2-dimethoxyethane or tetrahydrofuran, and at a temperature in the range, for example, 10° to 150° C., conveniently at or near 100° C.

Conveniently the reaction may be performed in the presence of a suitable catalyst, for example a metallic catalyst, for example palladium(O) or copper(I) such as tetrakis(triphenylphosphine)palladium, cuprous chloride or cuprous bromide.

A suitable protecting group for an amino group is, for example, an acyl group for example a (2–4C)alkanoyl group (especially acetyl), a (1–4C)alkoxycarbonyl group (especially methoxycarbonyl, ethoxycarbonyl or tert-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl or alkoxycarbonyl or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-charcoal.

A suitable protecting group for a hydroxy group is, for example, an acyl group, for example a (2–4C)alkanoyl group (especially acetyl), an aroyl group (especially benzoyl) or an arylmethyl group (especially benzyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-charcoal.

The preparation of starting materials of the formula $Ar^1$-$A^1$-$X^1$-H and of the formula II may be obtained by standard procedures of organic chemistry as illustrated in European Patent Applications Nos. 0375404, 0385662, 0409413 and 0420511.

(b) The coupling of a compound of the formula $Ar^1$-$A^1$-$X^1$-Z wherein Z is a displaceable group as defined hereinbefore, or alternatively, when $X^1$ is a thio group, Z may be a group of the formula $Ar^1$-$A^1$-$X^1$-, with an organometallic reagent of the formula III wherein M is an alkali metal or an alkaline earth metal such as lithium or calcium or M represents the magnesium halide portion of a conventional Grignard reagent; provided that, when there is an amino or hydroxy group in $Ar^1$ or on the phenylene group, or when Q is amino, any amino or hydroxy group may be protected by a conventional protecting group as defined hereinbefore or alternatively any such group need not be protected, whereafter any undesired protecting group in $Ar^1$, the phenylene group or Q is removed by conventional means.

The coupling reaction is conveniently performed in a suitable inert solvent as defined hereinbefore and at a temperature in the range, for example, –80° to +50° C., conveniently in the range –80° C. to ambient temperature.

The preparation of starting materials of the formula $Ar^1$-$A^1$-$X^1$-Z and of the formula III may be obtained by standard procedures of organic chemistry as illustrated in European Patent Applications Nos. 0375405, 0385662, 0409413 and 0420511.

(c) The coupling, preferably in the presence of a suitable base as defined hereinbefore, of a compound of the formula IV with a compound of the formula $Ar^1$-$A^1$-Z wherein Z is a displaceable group as defined hereinbefore; provided that, when there is an amino or hydroxy group in $Ar^1$ or on the phenylene group, or when Q is amino, any amino or hydroxy group may be protected by a conventional protecting group as defined hereinbefore or alternatively any such group need not be protected, whereafter any undesired protecting group in $Ar^1$, the phenylene group or Q is removed by conventional means.

The coupling reaction is conveniently performed in a suitable inert solvent as defined hereinbefore and at a temperature in the range, for example, 10° to 150° C., conveniently at or near 100° C. The reaction may conveniently be performed in the presence of a suitable catalyst as defined hereinbefore.

The starting materials of the formula $Ar^1$-$A^1$-Z and of the formula IV may be obtained by standard procedures of organic chemistry as illustrated in European Patent Applications Nos. 0375405, 0385662, 0409413 and 0420511. Starting materials of the formula IV are obtainable by analogous procedures to those illustrated in the accompanying Examples or by modifications thereto which are within the ordinary skill of an organic chemist.

(d) For the production of those compounds of the formula I wherein Q is cyano, nitro, formyl, thiazolyl or (2–4C)alkanoyl, the alkylation, preferably in the presence of a suitable base as defined hereinbefore, of a compound of the formula V with a compound of the formula $R^2$-Z wherein Z is a displaceable group as defined hereinbefore; provided that, when there is an amino or hydroxy group in $Ar^1$ or on the phenylene group, any amino or hydroxy group may be protected by a conventional protecting group as defined hereinbefore or alternatively any such group need not be protected, whereafter any undesired protecting group in $Ar^1$ or on the phenylene group is removed by conventional means.

The alkylation reaction is conveniently performed in a suitable inert solvent as defined hereinbefore and at a temperature in the range, for example, 10° to 150° C., conveniently at or near ambient temperature.

The starting materials of the formula V may be obtained by standard procedures of organic chemistry as illustrated in the accompanying Examples or by modifications thereto which are within the ordinary skill of an organic chemist.

(e) For the production of those compounds of the formula I wherein $X^1$ is a sulphinyl or sulphonyl group the oxidation of a compound of the formula I wherein $X^1$ is a thio group.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or tert-butyl methyl ether and at a temperature, for example, at or near ambient temperature, that is in the range 15° to 35° C. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as of the corresponding thio compound.

(f) For the production of those compounds of the formula I wherein $Ar^1$ bears an alkyl substituent on an available nitrogen atom, or wherein the phenylene group bears an alkoxy substituent, the alkylation of a compound of the formula I wherein $Ar^1$ bears a hydrogen atom on said available nitrogen atom, or wherein the phenylene group bears a hydroxy substituent.

A suitable alkylating agent is, for example, any agent known in the art for the alkylation of an available nitrogen atom, or of hydroxy to alkoxy, for example an alkyl halide, for example a (1–4C)alkyl chloride, bromide or iodide, in the presence of a suitable base. A suitable base for the alkylation reaction is, for example, an alkali or alkaline earth metal carbonate, sodium hydroxide, potassium hydroxide, sodium hydride or potassium hydride. The alkylation reaction is preferably performed in a suitable inert solvent or diluent, for example N,N-dimethylformamide, dimethylsulphoxide, acetone, 1,2-dimethoxyethane or tetrahydrofuran, and at a temperature in the range, for example, 10° to 150° C., conveniently at or near ambient temperature.

(g) For the production of those compounds of the formula I wherein $Ar^1$ bears one or more thioxo substituents, the reaction of a compound of the formula I wherein $Ar^1$ bears one or more oxo substituents with a thiation reagent such that each oxo substituent is converted into a thioxo substituent; provided that, when there is an amino or hydroxy group in $Ar^1$ or on the phenylene group, or when Q is amino, any such group may be protected by a conventional protecting group or alternatively any such group need not be protected, whereafter any undesired protecting group in $Ar^1$, the phenylene group or Q is removed by conventional means.

A suitable thiation reagent is, for example, any agent known in the art for the conversion of an oxo group to a thioxo group such as, for example, 2,4-bis-(4-methoxyphenyl)-1,3-dithia-2,4-diphosphetane-2,4-disulphide (Lawesson's Reagent) or phosphorus pentasulphide. The thiation reaction is generally carried out with the required stoichiometric amount of thiation reagent in order to reduce the risk of damage to other functional groups. In general the reaction is carried out in a suitable solvent or diluent such as toluene, xylene or tetrahydrofuran and at a temperature, for example, at or near the reflux temperature of the solvent or diluent, that is in the range 65° to 150° C.

When a pharmaceutically-acceptable salt of a compound of the formula I is required, it may be obtained, for example, by reaction of said compound with a suitable acid or base using a conventional procedure. When an optically active form of a compound of the formula I is required, it may be obtained by carrying out one of the aforesaid procedures using an optically active starting material, or by resolution of a racemic form of said compound using a conventional procedure.

As stated previously, the compounds of the formula I are inhibitors of the enzyme 5-LO. The effects of this inhibition may be demonstrated using one or more of the standard procedures set out below:

a) An in vitro assay system involving incubating a test compound with heparinised human blood, prior to challenge with the calcium ionophore A23187 and then indirectly measuring the inhibitory effects on 5-LO by assaying the amount of $LTB_4$ using specific radioimmunoassays described by Carey and Forder (F. Carey and R. A. Forder, *Prostaglandins, Leukotrienes Med.*, 1986, 22, 57; *Prostaglandins*, 198, 28, 666; *Brit. J. Pharmacol.* 1985, 84, 34P) which involve the use of a protein-$LTB_4$ conjugate produced using the procedure of Young et alia (*Prostaglandins*, 1983, 26(4), 605–613). The effects of a test compound on the enzyme cyclooxygenase (which is involved in the alternative metabolic pathway for arachidonic acid and gives rise to prostaglandins, thromboxanes and related metabolites) may be measured at the same time using the specific radioimmunoassay for thromboxane $B_2(TxB_2)$ described by Carey and Forder (see above). This test provides an indication of the effects of a test compound against 5-LO and also cyclooxygenase in the presence of blood cells and proteins. It permits the selectivity of the inhibitory effect on 5-LO or cyclooxygenase to be assessed.

b) An ex vivo assay system, which is a variation of test a) above, involving administration of a test compound (usually orally as the suspension produced when a solution of the test compound in dimethylsulphoxide is added to carboxymethylcellulose), blood collection, heparinisation, challenge with A23187 and radioimmunoassay of $LTB_4$ and $TxB_2$. This test provides an indication of the bioavailability of a test compound as an inhibitor of 5-LO or cyclooxygenase.

c) An in vivo system involving measuring the effects of a test compound administered orally against the liberation of $LTB_4$ induced by zymosan within an air pouch generated within the subcutaneous tissue of the back of male rats. The rats are anaesthetised and air pouches are formed by the injection of sterile air (20 ml). A further injection of air (10 ml) is similarly given after 3 days. At 6 days after the initial air injection the test compound is administered (usually orally as the suspension produced when a solution of the test compound in dimethylsulphoxide is added to hydroxypropylmethylcellulose), followed by the intrapouch injection of zymosan (1 ml of a 1% suspension in physiological saline). After 3 hours the rats are killed, the air pouches are lavaged with physiological saline, and the specific radioimmunoassay described above is used to assay $LTB_4$ in the washings. This test provides an indication of inhibitory effects against 5-LO in an inflammatory milieu.

Although the pharmacological properties of the compounds of the formula I vary with structural changes as expected, in general compounds of the formula I possess 5-LO inhibitory effects at the following concentrations or doses in at least one of the above tests a)–c):

Test a): $IC_{50}$ ($LTB_4$) in the range, for example, 0.01–40 µM $IC_{50}$ ($TxB_2$) in the range, for example, 40–200 µM;

Test b): oral $ED_{50}(LTB_4)$ in the range, for example, 0.1–100 mg/kg;

Test c): oral $ED_{50}(LTB_4)$ in the range, for example, 0.1–100 mg/kg.

No overt toxicity or other untoward effects are present in tests b) and/or c) when compounds of the formula I are administered at several multiples of their minimum inhibitory dose or concentration.

Thus, by way of example, the compound ethyl 2-ethyl-2-[3-(1-methyl-2-oxo-1,2-dihydroquinolin-6-ylmethoxy)phenyl]butyronitrile has an $IC_{50}$ of 0.5 µM against $LTB_4$ in test a); the compound 2-methyl-2-[3-(1-methyl-2-oxo-1,2-dihydroquinolin-6-ylmethoxy)phenyl]butyronitrile has an $IC_{50}$ of 0.08 µM in test a); the compound 2,2-diallyl-2-[3-(1-methyl-2-oxo-1,2-dihydroquinolin-6-ylmethoxy)phenyl]acetonitrile has an $IC_{50}$ of 0.05 µM in test a); and the compound 3-ethyl-3-[3-(1-methyl-2-oxo-1,2-dihydroquinolin-6-ylmethoxy)phenyl]pentan-2-one has an $IC_{50}$ of 0.15 µM in test a). In general those compounds of the formula I which are particularly preferred have an $IC_{50}$ of <1 µM against $LTB_4$ in test a).

These compounds are examples of compounds of the invention which show selective inhibitory properties for 5-LO as opposed to cyclooxygenase, which selective properties are expected to impart improved therapeutic properties, for example, a reduction in or freedom from the gastrointestinal side-effects frequently associated with cyclooxygenase inhibitors such as indomethacin.

According to a further feature of the invention there is provided a pharmaceutical composition which comprises an α,α-dialkylbenzyl derivative of the formula I, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of active ingredient (that is an α,α-dialkylbenzyl derivative of the formula I, or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided an α,α-dialkylbenzyl derivative of the formula I, or a pharmaceutically-acceptable salt thereof, for use in a method of treatment of the human or animal body by therapy.

The invention also includes a method of treating a disease or medical condition mediated alone or in part by one or more leukotrienes which comprises administering to a warm-blooded animal requiring such treatment an effective amount of an active ingredient as defined above. The invention also provides the use of such an active ingredient in the production of a new medicament for use in a leukotriene mediated disease or medical condition.

The size of the dose for therapeutic or prophylactic purposes of a compound of the formula I will naturally vary according to the nature and severity of the conditions, the age and sex of the animal or patient and the route of administration, according to well known principles of medicine. As mentioned above, compounds of the formula I are useful in treating those allergic and inflammatory conditions which are due alone or in part to the effects of the metabolites of arachidonic acid arising by the linear (5-LO catalysed) pathway and in particular the leukotrienes, the production of which is mediated by 5-LO. As previously mentioned, such conditions include, for example, asthmatic conditions, allergic reactions, allergic thiniris, allergic shock, psoriasis, atopic dermatitis, cardiovascular and cerebrovascular disorders of an inflammatory nature, arthritic and inflammatory joint disease, and inflammatory bowel diseases.

In using a compound of the formula I for therapeutic or prophylactic purposes it will generally be administered so that a daily dose in the range, for example, 0.5 mg to 75 mg per kg body weight is received, given if required in divided doses. In general lover doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used.

Although the compounds of the formula I are primarily of value as therapeutic agents for use in warm-blooded animals (including man), they are also useful whenever it is required to inhibit the enzyme 5-LO. Thus, they are useful as pharmacological standards for use in the development of new biological tests and in the search for new pharmacological agents.

By virtue of their effects on leukotriene production, the compounds of the formula I have certain cytoprotective effects, for example they are useful in reducing or suppressing certain of the adverse gastrointestinal effects of the cyclooxygenase inhibitory non-steroidal anti-inflammatory agents (NSAIA), such as indomethacin, acetylsalicylic acid, ibuprofen, sulindac, rolmerin and piroxicam. Furthermore, co-administration of a 5-LO inhibitor of the formula I with a NSAIA can result in a reduction in the quantity of the latter agent needed to produce a therapeutic effect, thereby reducing the likelihood of adverse side-effects. According to a further feature of the invention there is provided a pharmaceutical composition which comprises an α,α-dialkylbenzyl derivative of the formula I, or a pharmaceutically-acceptable salt thereof as defined hereinbefore, in conjunction or admixture with a cyclooxygenase inhibitory non-steroidal anti-inflammatory agent (such as those mentioned above), and a pharmaceutically-acceptable diluent or carrier.

The cytoprotective effects of the compounds of the formula I may be demonstrated, for example in a standard laboratory model which assesses protection against indomethacin-induced or ethanol-induced ulceration in the gastrointestinal tract of rats.

The compositions of the invention may in addition contain one or more therapeutic or prophylactic agents known to be of value for the disease under treatment. Thus, for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

The invention will now be illustrated in the following non-limiting Examples in which, unless otherwise stated:

(i) evaporations were carried out by rotary evaporation in vacuo and work-up procedures were carried out after removal of residual solids by filtration;

(ii) operations were carried out at room temperature, that is in the range 18°–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, W. Germany;

(iv) yields are given for illustration only and are not necessarily the maximum attainable;

(v) the end-products of the formula I have satisfactory microanalyses and their structures were confirmed by NMR and mass spectral techniques;

(vi) intermediates were not generally fully characterised and purity was assessed by thin layer chromatographic, infra-red (IR) or NMR analysis;

(vii) melting points are uncorrected and were determined using a Merrier SP62 automatic melting point apparatus or an oil-bath apparatus; melting points for the end-products of the formula I were determined after crystallisation from a conventional organic solvent such as ethanol, methanol, acetone, ether or hexane, alone or in admixture; and (viii) the following abbreviations have been used:

THF   tetrahydrofuran;

DMF   N,N-dimethylformamide.

EXAMPLE 1

A mixture of 2-ethyl-2-(3-hydroxyphenyl)butyronitrile (0.234 g), 6-bromomethyl-1-methyl-1,2-dihydroquinolin-2-one (1.1 equivalents: European Patent Application No. 0385662, Example 6 thereof), potassium carbonate (0.5 g) and DMF (10 ml) was stirred at ambient temperature for 68 hours. The mixture was partitioned between methylene chloride and water. The organic layer was washed with water and with brine, dried (MgSO$_4$) and evaporated. The residue was purified by column chromatography using a 1:1 v/v mixture of hexane and ethyl acetate as eluent. There was thus obtained 2-ethyl-2-[3-(1-methyl-2-oxo-1,2-dihydroquinolin-6-ylmethoxy)phenyl]butyronitrile (0.368 g, 78%), as an oil.

NMR Spectrum (CDCl$_3$, δ values) 0.90(t, 6H), 1.97(m, 4H), 3.74(s, 3H), 5.14(s, 2H), 6.74(d, 1H), 6.92(m, 1H), 6.97(m, 1H), 7.05(t, 1H), 7.33(m, 1H), 7.40(m, 1H), 7.65(m, 2H), 7.69(d, 1H).

The 2-ethyl-2-(3-hydroxyphenyl)butyronitrile used as a starting material was obtained as follows:

n-Butyl-lithium (1.6M in hexane, 18.8 ml) was added dropwise to a solution of di-isopropylamine (4.21 ml) in THF (100 ml) which had been cooled to −78° C. The mixture was stirred at −78° C. for 30 minutes. A solution of 3-methoxyphenylacetonitrile (4.18 ml) in THF (10 ml) was added dropwise and the mixture was stirred and allowed to warm to 0° C. The mixture was stirred at 0° C. for 15 minutes then recooled to −78° C. A solution of ethyl iodide (2.64 ml) in THF (10 ml) was added and the mixture was stirred for 16 hours and allowed to warm to ambient temperature. The mixture was acidified to pH4 by the addition of dilute aqueous hydrochloric acid and partitioned between ethyl acetate and water. The organic phase was washed with brine, dried (MgSO$_4$) and evaporated. The residue was purified by column chromatography using a 4:1 v/v mixture of hexane and ethyl acetate as eulent. There was thus obtained 2-(3-methoxyphenyl)butyronitrile (4.1 g, 78%) as an oil which was used without further purification.

A portion (0.875 g) of the product so obtained was alkylated with ethyl iodide using an analogous procedure to that described immediately above. There was thus obtained 2-ethyl-2-(3-methoxyphenyl)butyronitrile (0.721 g, 65%) as an oil.

A solution of a portion (0.609 g) of the product so obtained in methylene chloride (10 ml) was cooled in an ice-bath and boron tribromide (1M in methylene chloride, 6 ml) was added. The mixture was stirred at ambient temperature for 16 hours. The mixture was partitioned between diethyl ether and water. The organic extracts were combined and extracted with 2N aqueous sodium hydroxide solution. The aqueous extract was acidified with dilute aqueous hydrochloric acid and extracted with diethyl ether. The organic phase was washed with brine, dried (MgSO$_4$) and evaporated. The residue was purified by column chromatography using a 3:1 v/v mixture of hexane and ethyl acetate as eluent. There was thus obtained the required starting material (0.406 g, 72%) as an oil which was used without further purification.

EXAMPLE 2

The alkylation of 2-ethyl-2-(3-hydroxyphenyl)butyronitrile described in Example 1 was repeated except that 2-bromomethylnaphthalene was used in place of 6-bromomethyl-1-methyl-1,2-dihydroquinolin-2-one. There was thus obtained 2-ethyl-2-[3-(naphth-2-ylmethoxy)phenyl]butyronitrile in 96% yield, m.p. 108°–110° C.

EXAMPLE 3

In an analogous procedure to that described in Example 1, 2-bromomethylnaphthalene was reacted with ethyl 3-hydroxybenzoate to give ethyl 3-(naphth-2-ylmethoxy)benzoate in 85% yield, m.p. 45°–46.5° C.

A solution of the product so obtained (1.53 g) in diethyl ether (15 ml) was added to ethylmagnesium iodide [prepared from ethyl iodide (2.34 g) and magnesium (0.42 g) in diethyl ether (30 ml)]. The mixture was heated to reflux for 20 minutes. The mixture was cooled to ambient temperature and water (3 ml) was added, The mixture was partitioned between ethyl acetate and water. The organic phase was washed with brine, dried (MgSO$_4$) and evaporated. The residue was purified by column chromatography using increasingly polar mixtures of hexane and ethyl acetate as eluent. There was thus obtained 3-[3-(naphth-2-ylmethoxy)phenyl]pentan-3-ol (1.3 g, 81%) m.p. 60°–63° C.

Sodium hydride (50% w.w. dispersion in mineral oil; 0.05 g) was added portionwise to a solution of a portion (0.25 g) of the propan-1-ol so obtained in DMF (5 ml) and the mixture was stirred at ambient temperature for 10 minutes. Methyl iodide (0.1 ml) was added and the mixture was stirred at ambient temperature for 50 hours. The mixture was partitioned between ethyl acetate and water. The organic phase was washed with brine, dried (MgSO$_4$) and evaporated. The residue was purified by column chromatography using increasingly polar mixtures of hexane and ethyl acetate as eluent. There was thus obtained methyl 3-[3-(naphth-2-ylmethoxy)phenyl]pent-3-yl ether (0.09 g, 35%), m.p. 70°–72° C. (recrystallised from hexane).

EXAMPLE 4

The alkylation of 2-ethyl-2-(3-hydroxyphenyl)butyronitrile as described in Example 1 was repeated except that 2-chloromethylquinoline hydrochloride was used in place of 6-bromomethyl-1-methyl-1,2-dihydroquinolin-2-one. There was thus obtained 2-ethyl-2-[3-(2-quinolylmethoxy)phenyl] butyronitrile in 69% yield, m.p. 66°–67° C.

NMR Spectrum (CDCl$_3$, δ values) 0.87(t, 6H), 1.94(m, 4H), 5.40(s, 2H), 6.56(m, 1H), 7.01(m, 1H), 7.08(m, 1H), 7.30(t, 1H), 7.56(m, 1H), 7.69(d, 1H), 7.75(m, 1H), 7.84(m, 1H), 8.08(m, 1H), 8.20(d, 1H).

EXAMPLE 5

The reaction described in Example 1 was repeated except that 2-(3-hydroxyphenyl)-2-methylbutyronitrile was used in place of 2-ethyl-2-(3-hydroxyphenyl)butyronitrile. There was thus obtained 2-methyl-2-[3-(1-methyl-2-oxo-1,2-dihydroquinolin-6-ylmethoxy)phenyl]butyronitrile in 45% yield as a gum.

NMR Spectrum (CDCl$_3$, δ values) 0.96(t, 3H), 1.69(s, 3H), 1.95(m, 2H), 3.73(s, 3H), 5.14(s, 2H), 6.74(d, 1H), 6.92(m, 1H), 7.03(m, 1H), 7.10(m, 1H), 7.31(t, 1H), 7.40(d, 1H), 7.65(m, 2H), 7.69(d, 1H).

The 2-(3-hydroxyphenyl)-2-methylbutyronitrile used as a starting material was obtained as follows:

The procedures described in the portion of Example 1 which is concerned with the preparation of starting materials were repeated except that 3-methoxyphenylacetonitrile was alkylated in turn with methyl iodide and ethyl iodide. The 2-(3-methoxyphenyl)-2-methylbutyronitrile so obtained was treated with boron tribromide to give the required starting material in an overall yield of 8% as a gum.

NMR Spectrum (CDCl$_3$, δ values) 0.97(t, 3H), 1.69(s, 3H), 1.95(m, 2H), 5.11(s, 1H), 6.77(m, 1H), 6.94(m, 1H), 6.97(m, 1H), 7.25(t, 1H).

EXAMPLE 6

The reaction described in Example 1 was repeated except that 2-allyl-2-(3-hydroxyphenyl)butyronitrile was used in place of 2-ethyl-2-(3-hydroxyphenyl)butyronitrile. There were thus obtained 2-allyl-2-[3-(1-methyl-2-oxo-1,2-dihydroquinolin-6-ylmethoxy)phenyl]butyronitrile in 16% yield as a gum.

NMR Spectrum (CDCl$_3$, δ values) (0.91(t, 3H), 1.98(m, 2H), 2.65(d, 2H), 3.73(s, 3H), 5.13(m, 1H), 5.14(s, 2H), 5.64(m, 1H), 6.73(d, 1H), 6.92(m, 1H), 6.96(m, 1H), 7.05(m, 1H), 7.32(t, 1H), 7.40(d, 1H), 7.62(m, 2H), 7.65(d, 1H).

The 2-allyl-2-(3-hydroxyphenyl)butyronitrile used as a starting material was obtained as follows:

The procedures described in the portion of Example 1 which is concerned with the preparation of starting materials were repeated except that 3-methoxyphenylacetonitrile was alkylated in turn with ethyl iodide and allyl bromide. The 2-allyl-2-(3-methoxyphenyl)butyronitrile so obtained was treated with boron tribromide to give the required starting material in an overall yield of 46% as a gum.

NMR Spectrum (CDCl$_3$, δ values) 0.93(t, 3H), 1.99(m, 2H), 2.64(d, 2H), 5.10(m, 1H), 5.17(m, 1H), 5.27(s, 1H), 5.66(m, 1H), 6.78(m, 1H), 6.93(m, 1H), 6.94(m, 1H), 7.26(t, 1H).

EXAMPLE 7

The reaction described in Example 1 was repeated except that 2,2-diallyl-2-(3-hydroxyphenyl)acetonitrile was used in place of 2-ethyl-2-(3-hydroxyphenyl)butyronitrile. There was thus obtained 2,2-diallyl-2-[3-(1-methyl-2-oxo-1,2-dihydroquinolin-6-ylmethoxy)phenyl]acetonitrile in 7% yield as a gum.

NMR Spectrum (CDCl$_3$, δ values) 2.68(m, 4H), 3.73(s, 3H), 5.09(s, 2H), 5.14(s, 2H), 5.16(m, 2H), 5.64(m, 2H), 6.73(d, 1H), 6.92(m, 1H), 6.99(m, 1H), 7.06(m, 1m), 7.31(t, 1H), 7.39(m, 1H), 7.55(m, 2H), 7.59(d, 1H).

The 2,2-diallyl-2-(3-hydroxyphenyl)acetonitrile used as a starting material was obtained as follows:

The procedures described in the portion of Example 1 which is concerned with the preparation of starting materials were repeated except that 3-methoxyphenylacetonitrile was alkylated with allyl bromide. The 2,2-diallyl-2-(3-methoxyphenyl)acetonitrile so obtained was treated with boron tribromide to give the required starting material in an overall yield of 39% as an oil.

NMR Spectrum (CDCl$_3$, δ values) 2.68(d, 4H), 5.11(m, 2H), 5.18(m, 2H), 5.65(m, 2H), 6.78(m, 1H), 6.93(m, 1H), 6.94(m, 1H), 7.25(t, 1H).

EXAMPLE 8

The procedure described in the last paragraph of Example 3 was repeated except that ethyl iodide was used in place of methyl iodide. There was thus obtained ethyl 3-[3-(naphth-2-ylmethoxy)phenyl]pent-3-yl ether in 51% yield, m.p. 45°–47° C.

EXAMPLE 9

Using an analogous procedure to that described in Example 1, 6-bromomethyl-1-methyl-1,2-dihydroquinolin-2-one was reacted with 3-ethyl-3-(3-hydroxyphenyl)pentan-2-one to give 3-ethyl-3-[3-(1-methyl-2-oxo-1,2-dihydroquinolin-6-ylmethoxy)phenyl]pentan-2-one in 40% yield as a gum.

NMR Spectrum (CDCl$_3$, δ values) 0.67(t, 6H), 1.98(m, 4H), 3.73(s, 3H), 5.10(s, 2H), 6.74(d, 1H), 6.83(m, 1H), 6.84(m, 1H), 6.88(m, 1H), 7.27(t, 1H), 7.39(d, 1H), 7.63(m, 2H), 7.69(d, 1H).

The 3-ethyl-3-(3-hydroxyphenyl)pentan-2-one used as a starting material was obtained as follows:

An excess of oxalyl chloride was added dropwise to a stirred mixture of 3-methoxyphenylacetic acid (33.2 g), DMF (4 ml) and methylene chloride (800 ml) and the mixture was stirred at ambient temperature for 65 hours. The mixture was evaporated to leave 3-methoxyphenylacetyl chloride (39.6 g).

Triethylamine (44.4 g) was added portionwise to a stirred mixture of 3-methoxyphenylacetyl chloride (36.9 g), N,O-dimethylhydroxylamine hydrochloride (21.5 g) and methylene chloride (500 ml) which had been cooled to 0° C. The mixture was stirred at 5° C. for 90 minutes and at ambient temperature for 65 hours. The mixture was washed in turn with dilute aqueous hydrochloric acid, a saturated aqueous sodium bicarbonate solution and brine, dried (MgSO$_4$) and evaporated. The residue was purified by column chromatography using a 1:1 v/v mixture of hexane and ethyl acetate as eluent. There was thus obtained N,O-dimethyl-3-methoxyphenylacetohydroxamic acid (29 g) as an oil.

Methylmagnesium iodide [prepared from magnesium (6.8 g) and methyl iodide (39.8 g) in diethyl ether (200 ml)] was added to a stirred solution of the hydroxamic acid so obtained in THF (500 ml) which had been cooled to 5° C. The mixture was stirred at ambient temperature for 65 hours. The mixture was partitioned between diethyl ether and a saturated aqueous ammonium chloride solution. The organic phase was washed with brine, dried (MgSO$_4$) and evaporated. The residue was purified by column chromatography using a 2:1 v/v mixture of hexane and ethyl acetate as eluent. There was thus obtained 1-(3-methoxyphenyl)propan-2-one (13.2 g) as an oil.

NMR Spectrum (CDCl$_3$, δ values) 2.14(s, 3H), 3.65(s, 2H), 3.80(s, 3H), 6.80(m, 2H), 7.24(t, 1H).

Using analogous procedures to those described in the portion of Example 1 which is concerned with the preparation of starting materials, 1-(3-methoxyphenyl)propan-2-one was alkylated with ethyl iodide and the 3-ethyl-3-(3-methoxyphenyl)pentan-2-one so obtained in 5% yield was treated with boron tribromide to give 3-ethyl-3-(3-hydroxyphenyl)pentan-2-one in 44% yield as an oil.

NMR Spectrum (CDCl$_3$, δ values) 0.68(t, 6H), 1.89(s, 3H), 1.98(m, 4H), 5.28(m, 1H), 6.68(m, 1H), 6.75(m, 1H), 6.79(m, 1m), 7.22(t, 1H).

EXAMPLE 10

A solution of 1-[3-(naphth-2-ylmethoxy)phenyl]propan-2-one (1.45 g) in THF (10 ml) was added dropwise to a stirred mixture of sodium hydride [50% w/w dispersion in mineral oil, 0.48 g; washed with petroleum ether (b.p. 40°–60° C.) to remove the mineral oil] in N-methylpyrrolidin-2-one (10 ml). The resultant mixture was stirred at ambient temperature for 30 minutes. The mixture was cooled to 10° C. and a solution of allyl bromide (1.21 g) in THF (5 ml) was added dropwise. The mixture was stirred at ambient temperature for 1 hour. Water was added and the mixture was acidified to pH 5 by the addition of dilute hydrochloric acid. The mixture was extracted with diethyl ether. The organic extract was washed with water and with brine, dried ($MgSO_4$) and evaporated. The residue was purified by column chromatography using a 4:1 v/v mixture of petroleum ether (b.p. 40°–60° C.) and methylene chloride as eluent. There was thus obtained 1,1-diallyl-1-[3-(naphth-2-ylmethoxy)phenyl]propan-2-one (1.5 g, 68%), m.p. 73°–74° C.

NMR Spectrum ($CDCl_3$, δ values) 1.86(s, 3H), 2.17(d, 4H), 4.8–5.7(m, 8H), 6.65–8.0(m, 11H).

The 1-[3-(naphth-2-ylmethoxy)phenyl]propan-2-one used as a starting material was obtained as follows:

A mixture of 2-bromomethylnaphthalene (19.5 g), 3-hydroxyphenylacetic acid (6.09 g), potassium carbonate (22 g) and acetone (100 ml) was stirred and heated to reflux for 6 hours. The mixture was cooled, filtered and evaporated. A mixture of the residue, 2N sodium hydroxide solution (125 ml) and ethanol (30 ml) was heated to reflux for 2 hours. The solution was cooled, washed with diethyl ether and acidified to pH4 by the addition of concentrated aqueous hydrochloric acid. The precipitate was isolated and dried. There was thus obtained 3-(naphth-2-ylmethoxy)phenylacetic acid in 94% yield, m.p. 142°–143° C.

Methyl-lithium (1.4M in diethyl ether, 35.7 ml) was added dropwise to a stirred mixture of a portion (2.92 g) of the phenylacetic acid so obtained, lithium iodide (1.34 g) and diethyl ether (100 ml) and the resultant mixture was stirred at ambient temperature for 2 hours. Aniline (0.003 ml) was added and the mixture was partitioned between diethyl ether and a dilute aqueous hydrochloric acid solution. The organic phase was washed with water, with a saturated aqueous sodium thiosulphate solution, with a saturated sodium bicarbonate solution and with brine, dried ($MgSO_4$) and evaporated. The residue was purified by column chromatography using methylene chloride as eluent. There was thus obtained the required starting material (1 g, 34%), m.p. 48°–49° C.

NMR Spectrum ($CDCl_3$, δ values) 2.1(s, 3H), 3.63(s, 2H), 5.2(s, 2H), 6.4–8.0(m, 11H).

EXAMPLE 11

A solution of 2-[1-(5-fluoro-3-(naphth-2-ylmethoxy)phenyl)propyl]thiazole (0.754 g) in THF (20 ml) was added to a stirred suspension of potassium hydride (35% w/w dispersion in mineral oil, 0.1 g) in THF (6 ml) and the mixture was stirred at ambient temperature for 2 hours. Ethyl iodide (0.39 g) was added and the mixture was stirred at ambient temperature for 16 hours. The mixture was partitioned between ethyl acetate and a saturated aqueous ammonium chloride solution. The organic phase was washed with brine, dried ($MgSO_4$) and evaporated. The residue was purified by column chromatography using a 3:1 v/v mixture of hexane and ethyl acetate as eluent. There was thus obtained 2-[3-(5-fluoro-3-(naphth-2-ylmethoxy)phenyl)pent-3-yl]thiazole (0.255 g, 31%), m.p. 81°–82° C.

NMR Spectrum ($CDCl_3$, δ values) 0.73(t, 6H), 2.27(m, 4H), 5.16(s, 2H), 6.6(m, 2H), 6.72(m, 1H), 7.18(d, 1H), 7.5(m, 1H), 7.66(d, 1H), 7.85(m, 4H).

The 2-[1-(5-fluoro-3-(naphth-2-ylmethoxy)phenyl)propyl]thiazole used as a starting material was obtained as follows:

Sodium hydride (60% w/v dispersion in mineral oil, 4.64 g) was added portionwise to a stirred solution of 2-naphthalenemethanol (18.35 g) in N,N-dimethylacetamide (400 ml) and the mixture was stirred at ambient temperature for 45 minutes. A solution of 3,5-difluorobenzonitrile (16.1 g) in N,N-dimethylacetamide (100 ml) was added and the mixture was stirred at ambient temperature for 66 hours. The mixture was evaporated and the residue was partitioned between methylene chloride and water. The organic phase was washed with brine, dried ($MgSO_4$) and evaporated. The residue was crystallised under ethanol. There was thus obtained 5-fluoro-3-(naphth-2-ylmethoxy)benzonitrile (23.5 g), m.p. 92°–93° C.

A solution of 2-bromothiazole (2.33 ml) in diethyl ether (25 ml) was added to a stirred mixture of n-butyl-lithium (1.6M in hexane, 16.13 ml) and diethyl ether (10 ml) which had been cooled to –75° C. The mixture was stirred at –75° C. for 75 minutes. A solution of 5-fluoro-3-(naphth-2-ylmethoxy)benzonitrile (7.18 g) in THF (25 ml) was added and the mixture was stirred at –75° C. for 30 minutes. A saturated solution of hydrogen chloride in diethyl ether was added and the acidified mixture was allowed to warm to ambient temperature. The mixture was partitioned between methylene chloride and water. The organic phase was washed with water and with brine, dried ($MgSO_4$) and evaporated. The residue was recrystallised from ethanol. There was thus obtained 5-fluoro-3-(naphth-2-ylmethoxy)phenyl 2-thiazolyl ketone (7.17 g), 118°–119° C.

NMR Spectrum ($CDCl_3$, δ values) 5.31(s, 2H), 7.01(m, 1H), 7.5(m, 2H), 7.56(m, 1H), 7.73(d, 1H), 7.9(m, 5H), 8.01(t, 1H), 8.06(d, 1H).

A mixture of a portion (2.72 g) of the compound so obtained, ethyltriphenylphosphonium bromide (2.78 g), potassium carbonate (2.59 g) and 1,4-dioxan (50 ml) was stirred and heated to reflux for 5 days. The mixture was cooled to ambient temperature and partitioned between ethyl acetate and water. The organic phase was washed with brine, dried ($MgSO_4$) and evaporated. The residue was purified by column chromatography using a 3:1 v/v mixture of hexane and ethyl acetate as eluent. There was thus obtained 5-fluoro-3-(naphth-2-ylmethoxy)-β-methyl-α-(2-thiazolyl) styrene (1.2 g), as a mixture of (E)- and (Z)-isomers.

After appropriate repetition of the above-described reactions, a mixture of the isomers (27.77 g), 30% palladium-on-charcoal catalyst (9.29 g) and ethanol (200 ml) was stirred under an atmosphere of hydrogen for 2 days. A further portion of catalyst (9.29 g) was added and the reaction was continued for a second period of 2 days. A further portion of catalyst (9.29 g) was added and the reaction was continued for a further 2 days. The mixture was filtered and the filtrate was evaporated. The residue was partitioned between methylene chloride and a saturated aqueous sodium bicarbonate solution. The aqueous phase was acidified by the addition of concentrated aqeuous hydrochloric acid and extracted with methylene chloride. The organic solutions were combined, washed with brine, dried ($MgSO_4$) and evaporated. There was thus obtained 2-[1-(5-fluoro-3-hydroxyphenyl)propyl]thiazole (6.61 g), m.p. 86°–89° C.

A mixture of a portion (2.37 g) of the thiazole so obtained, 2-bromomethylnaphthalene (2.21 g), potassium carbonate (4 g) and DMF (100 ml) was stirred at ambient temperature for 18 hours. The mixture was evaporated and the residue was partitioned between methylene chloride and water. The organic phase was washed with brine, dried (MgSO₄) and evaporated. The residue was purified by column chromatography using a 3:1 v/v mixture of hexane and ethyl acetate as eluent. There was thus obtained 2-[1-(5-fluoro-3-(naphth-2-ylmethoxy)phenyl)propyl]thiazole (3.15 g) as a gum.

NMR Spectrum (CDCl₃, δ values) 0.92(t, 3H), 2.08(m, 1H), 2.31(m, 1H), 4.14(t, 1H), 5.18(s, 2H), 6.62(m, 1H), 6.67(m, 1H), 6.80(t, 1H), 7.16(d, 1H), 7.50(m, 3H), 7.68(d, 1H), 7.85(m, 4H).

EXAMPLE 12

A mixture of 6-bromomethyl-1-methyl-1,2-dihydroquinolin-2-one (0.296 g), 2-[3-(3-tert-butyldimethylsilyloxy-5-fluorophenyl)pent-3-yl]thiazole (0.447 g), potassium fluoride (0.136 g) and DMF (10 ml) was stirred at ambient temperature for 16 hours. The mixture was evaporated and the residue was partitioned between methylene chloride and water. The organic phase was washed with brine, dried (MgSO₄) and evaporated. The residue was purified by column chromatography using a 2:1 v/v mixture of hexane and ethyl acetate as eluent. There was thus obtained 2-[3-(5-fluoro-3-(1-methyl-2-oxo-1,2-dihydroquinolin-6-ylmethoxy)phenyl)pent-3-yl] thiazole (0.102 g) as a gum.

NMR Spectrum (CDCl₃, δ values) 0.75(t, 6H), 2.28(m, 4H), 3.73(s, 3H), 5.05(s, 2H), 6.55(m, 1H), 6.63(m, 1H), 6.69(m, 1H), 6.74(d, 1m), 7.22(d, 1H), 7.37(d, 1H).

The 2-[3-(3-tert-butyldimethylsilyloxy-5-fluorophenyl)pent-3-yl]thiazole used as a starting material was obtained as follows:

A mixture of 2-[1-(5-fluoro-3-hydroxyphenyl)propyl] thiazole (2.37 g) tert-butyldimethylsilyl chloride (1.57 g) imidazole (0.75 g) and DMF (100 ml) was stirred at ambient temperature for 17 hours. The mixture was evaporated and the residue was partitioned between methylene chloride and water. The organic phase was washed with brine, dried (MgSO₄) and evaporated. The residue was purified by column chromatography using a 3:1 v/v mixture of hexane and ethyl acetate as eluent. There was thus obtained 2-[1-(3-tert-butyldimethylsilyloxy-5-fluorophenyl)propyl]thiazole (2.16 g) as an oil.

A portion (1.06 g) of the compound so obtained was reacted with ethyl iodide using an analogous procedure to that described in Example 11. There was thus obtained 2-[3-(3-tert-butyldimethylsilyloxy-5-fluorophenyl)pent-3-yl] thiazole (0.454 g) as an oil.

NMR Spectrum (CDCl₃, δ values) 0.15(m, 6H), 0.76(t, 6H), 0.95(m, 9H), 2.28(m, 4H), 6.41(m, 1H), 6.52(m, 1H), 6.63(m, 1H), 7.25(d, 1H), 7.71(d, 1H).

EXAMPLE 13

The reaction described in Example 1 was repeated except that 2-benzyl-2-(3-hydroxyphenyl)butyronitrile was used in place of 2-ethyl-2-(3-hydroxphenyl)butyronitrile. There was thus obtained 2-benzyl-2-[3-(1-methyl-2-oxo-1,2-dihydroquinolin-6-ylmethoxy)phenyl]butyronitrile in 33% yield as a glass.

NMR Spectrum (CDCl₃, δ values) 0.93(t, 3H), 2.08(q, 2H), 3.15(q, 2H), 3.73(s, 3H), 5.07(s, 2H), 6.74(d, 1H), 6.95(m, 5H), 7.18(m, 3H), 7.25(m, 1H), 7.35(m, 1H), 7.63(m, 2H), 7.69(d, 1H).

The 2-benzyl-2-(3-hydroxyphenyl)butyronitrile used as a starting material was obtained as follows:

The procedures described in the portion of Example 1 which is concerned with the preparation of starting materials were repeated except that 3-methoxyphenylacetonitrile was alkylated in turn with ethyl iodide and benzyl bromide. The 2-benzyl-2-(3-methoxyphenyl)butyronitrile so obtained was treated with boron tribromide to give the required starting material in an overall yield of 20% as a gum.

NMR Spectrum (CDCl₃, δ values) 0.94(t, 3H), 2.08(q, 2H), 3.14(q, 2H), 5.35(broad hump, 1H), 6.90(m, 4H), 7.20(m, 5H).

CHEMICAL FORMULAE

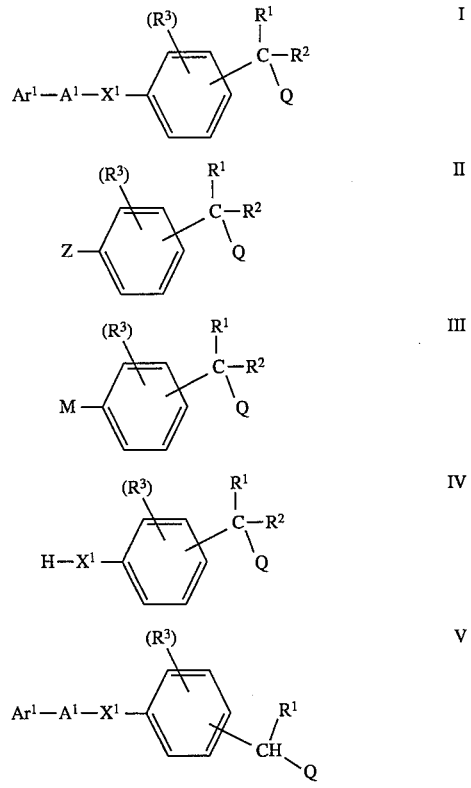

We claim:
1. An α,α-dialkylbenzyl derivative of the formula I

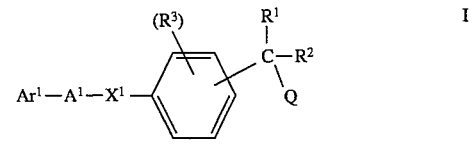

wherein $Ar^1$ is a 10-membered bicyclic heterocyclic moiety containing one or two nitrogen heteroatoms in one ring and optionally containing a further nitrogen heteroatom in the second ring, and $Ar^1$ may optionally bear up to four substituents selected from halogeno, hydroxy, cyano, oxo, thioxo, (1–4C)alkyl, (1–4C)alkoxy, fluoro-(1–4C)alkyl, phenyl, benzoyl, phenyl-(1–4C)alkyl, α,α-difluorobenzyl, α-hydroxybenzyl and α-[(1–4C)alkoxy]benzyl and wherein said phenyl substituent or any of said substituents which contain a phenyl group may optionally bear a substituent selected from halogeno, (1–4C)alkyl and (1–4C)alkoxy;

$A^1$ is a direct link to $X^1$ or is (1–3C)alkylene;

$X^1$ is oxy, thio, sulphinyl or sulphonyl;

the phenylene group may optionally bear one or two substituents $R^3$ selected from halogeno, hydroxy, amino, nitro, cyano, carbamoyl, ureido, (1–4C)alkyl, (1–4C)alkoxy and fluoro-(1–4C)alkyl;

each of $R^1$ and $R^2$, which may be the same or different is (1–4C)alkyl, (2–4C)alkenyl, (2–4C)alkynyl, fluoro-(1–4C)alkyl, phenyl or phenyl-(1–4C)alkyl and wherein said phenyl or phenyl-(1–4C)alkyl group may optionally bear one or two substituents selected from halogeno, trifluoromethyl, (1–4C)alkyl and (1–4C)alkoxy, provided that both of $R^1$ and $R^2$ are not methyl or fluoromethyl; and Q is cyano, amino, nitro, formyl, (1–4C)alkoxy, thiazolyl or (2–4C)alkanoyl;

or a pharmaceutically-acceptable salt thereof.

2. An α,α-dialkylbenzyl derivative of the formula I as claimed in claim 1 wherein $Ar^1$ is 2-quinolyl, 6-quinolyl, 6-quinoxazinyl, 2-oxo-1,2-dihydroquinolin-3-yl, 2-oxo-1,2-dihydroquinolin-6-yl, 2-oxo-1,2-dihydroquinolin-7-yl, 3-oxo-2,3-dihydro-4H-1,4-benzoxazin-7-yl or 3-oxo-2,3-dihydro-4H-1,4-benzothiazin-7-yl, which may optionally bear one, two or three substituents selected from fluoro, chloro, methyl, ethyl, 2-fluoroethyl, phenyl and benzyl;

$A^1$ is a direct link to $X^1$, or is methylene;

$X^1$ is oxy, thio, sulphinyl or sulphonyl;

the phenylene group is 1,3-phenylene which may optionally bear one substituent $R^3$ selected from fluoro, chloro and trifluoromethyl;

each of $R^1$ and $R^2$, which may be the same or different, is methyl ethyl, propyl, allyl or benzyl, provided that both of $R^1$ and $R^2$ are not methyl; and Q is cyano, methoxy, ethoxy, 2-thiazolyl, acetyl or propionyl;

or a pharmaceutically-acceptable salt thereof.

3. An α,α-dialkylbenzyl derivative of the formula I as claimed in claim 1 wherein $Ar^1$ is 2-quinolyl or 1-methyl-2-oxo-1,2-dihydroquinolin-6-yl;

$A^1$ is methylene and $X^1$ is oxy;

the phenylene group bearing $R^3$ is 1,3-phenylene or 5-fluoro-1,3-phenylene;

$R^1$ is ethyl or allyl;

$R^2$ is methyl, ethyl, allyl or benzyl; and

Q is cyano or acetyl;

or a pharmaceutically-acceptable salt thereof.

4. A specific compound of the formula I, or a pharmaceutically-acceptable salt thereof as claimed in claim 1 selected from:

ylmethoxy)phenyl]butyronitrile, 2-ethyl-2-[3-(1-methyl-2-oxo-1,2-dihydroquinolin-6-ylmethoxy)phenyl]butyronitrile, 2-methyl-2-[3-(1-methyl-2-oxo-1,2-dihydroquinolin-6-ylmethoxy)phenyl]butyronitrile, 2,2-diallyl-2-[3-(1-methyl-2-oxo-1,2-dihydroquinolin-6-ylmethoxy)phenyl]acetonitrile and 3-ethyl-3-[3-(1-methyl-2-oxo-1,2-dihydroquinolin-6-ylmethoxy)phenyl]pentan-2-one.

5. A process for the preparation of an α,α-dialkylbenzyl derivative of the formula I, or a pharmaceutically-acceptable salt thereof, as claimed in claim 1 which comprises:

(a) the coupling of a compound of the formula $Ar^1$-$A^1$-$X^1$-H with a compound of the formula II

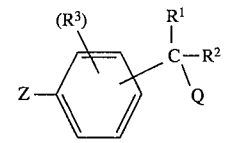

wherein Z is a displaceable group; provided that, when there is an amino or hydroxy group in $Ar^1$ or on the phenylene group, or when Q is amino, any amino or hydroxy group may be protected by a conventional protecting group or alternatively any such group need not be protected, whereafter any undesired protecting group in $Ar^1$, the phenylene group or Q is removed by conventional means;

(b) the coupling of a compound of the formula $Ar^1$-$A^1$-$X^1$-Z wherein Z is a displaceable group, or alternatively, when $X^1$ is a thio group, Z may be a group of the formula $Ar^1$-$A^1$-$X^1$-, with an organometallic reagent of the formula III

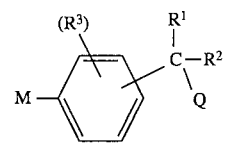

wherein M is an alkali metal or an alkaline earth metal such as lithium or calcium or M represents the magnesium halide portion of a conventional Grignard reagent; provided that, when there is an amino or hydroxy group in $Ar^1$ or on the phenylene group, or when Q is amino, any amino or hydroxy group may be protected by a conventional protecting group or alternatively any such group need not be protected, whereafter any undesired protecting group in $Ar^1$, the phenylene group or Q is removed by conventional means; or (c) the coupling of a compound of the formula IV

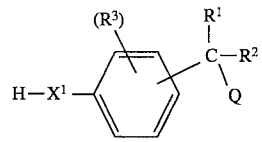

with a compound of the formula $Ar^1$-$A^1$-Z wherein Z is a displaceable group; provided that, when there is an amino or hydroxy group in $Ar^1$ or on the phenylene group, or when Q is amino, any amino or hydroxy group may be protected by a conventional protecting group or alternatively any such group need not be protected, whereafter any undesired protecting group in $Ar^1$, the phenylene group or Q is removed by conventional means; and (d) for the production of those compounds of the formula I wherein Q is cyano, nitro, formyl, thiazolyl or (2–4C)alkanoyl, the alkylation of a compound of the formula V

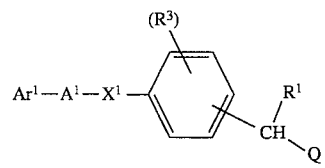

with a compound of the formula $R^2$-Z wherein Z is a displaceable group; provided that, when there is an amino or hydroxy group in $Ar^1$ or on the phenylene group, any amino or hydroxy group may be protected by a conventional protecting group or alternatively any such group need not be protected, whereafter any undesired protecting group in $Ar^1$ or on the phenylene group is removed by conventional means;

(e) for the production of those compounds of the formula I wherein $X^1$ is a sulphinyl or sulphonyl group the oxidation of a compound of the formula I wherein $X^1$ is a thio group;

(f) for the production of those compounds of the formula I wherein $Ar^1$ bears an alkyl substituent on an available nitrogen atom, or wherein the phenylene group bears an alkoxy substituent, the alkylation of a compound of the formula I wherein $Ar^1$ bears a hydrogen atom on said available nitrogen atom, or wherein the phenylene group bears a hydroxy substituent;

(g) for the production of those compounds of the formula I wherein $Ar^1$ bears one or more thioxo substituents, the reaction of a compound of the formula I wherein $Ar^1$ bears one or more oxo substituents with a thiation reagent such that each oxo substituent is converted into a thioxo substituent; provided that, when there is an amino or hydroxy group in $Ar^1$ or on the phenylene group, or when Q is amino, any such group may be protected by a conventional protecting group or alternatively any such group need not be protected, whereafter any undesired protecting group in $Ar^1$, the phenylene group or Q is removed by conventional means;

and when a pharmaceutically-acceptable salt of a compound of the formula I is required, it may be obtained by reaction of said compound with a suitable acid or base using a conventional procedure; and when an optically active form of a compound of the formula I is required, it may be obtained by carrying out one of the aforesaid procedures using an optically active starting material, or by resolution of a racemic form of said compound using a conventional procedure.

6. A pharmaceutical composition which comprises an $\alpha,\alpha$-dialkylbenzyl derivative of the formula I, or a pharmaceutically-acceptable salt thereof, as claimed in any one of claims 1 and 3–6 in association with a pharmaceutically-acceptable diluent or carrier.

7. A method of treating a disease or medical condition mediated alone or in part by one or more leukotrienes which comprises administering to a warm-blooded animal requiring such treatment an effective amount of an $\alpha,\alpha$-dialkylbenzyl derivative of the formula I, or a pharmaceutically-acceptable salt thereof, as claimed in any one of claims 1 and 3–6.

* * * * *